United States Patent
Hahn et al.

(10) Patent No.: US 7,207,983 B2
(45) Date of Patent: Apr. 24, 2007

(54) SYSTEM AND METHOD FOR REAL-TIME FEEDBACK OF ABLATION RATE DURING LASER REFRACTIVE SURGERY

(75) Inventors: David Worthington Hahn, Gainesville, FL (US); Brian T. Fisher, Sarasota, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 105 days.

(21) Appl. No.: 11/119,174

(22) Filed: Apr. 29, 2005

(65) Prior Publication Data

US 2006/0247608 A1  Nov. 2, 2006

(51) Int. Cl.
  *A61B 18/20* (2006.01)
(52) U.S. Cl. .................... 606/5; 606/4; 606/10
(58) Field of Classification Search ............. 606/4–6, 606/10–12; 351/205–212
  See application file for complete search history.

(56) References Cited

U.S. PATENT DOCUMENTS

| | | | |
|---|---|---|---|
| 6,271,914 B1 | 8/2001 | Frey et al. | |
| 6,271,915 B1 | 8/2001 | Frey et al. | |
| 6,325,792 B1* | 12/2001 | Swinger et al. | 606/4 |
| 6,547,393 B2* | 4/2003 | Ruiz | 351/212 |
| 6,635,051 B1* | 10/2003 | Hohla | 606/5 |
| 6,702,809 B1 | 3/2004 | Knopp et al. | |
| 6,964,659 B2* | 11/2005 | Gross et al. | 606/5 |
| 7,044,602 B2* | 5/2006 | Chernyak | 351/208 |
| 7,083,609 B2* | 8/2006 | Chernyak | 606/5 |
| 2002/0169441 A1 | 11/2002 | Lemberg | |
| 2003/0174281 A1 | 9/2003 | Herekar et al. | |

FOREIGN PATENT DOCUMENTS

WO  WO 02/38323 A1  5/2002

OTHER PUBLICATIONS

Pettit et al. "Excimer Laser Corneal Ablation: Absense of a Significant Incubation Effect", 1991, Lasers in Surgery and Medicine, 11:411-418.
Ediger et al. "Noninvasive Monitoring of Excimer Laser Ablation by Time-Resolved Reflectometry", 1993, Refractive and Corneal Surgery, 9:268-275.
Pettit et al. "Dynamic Optical Properties of Collagen-Based Tissue During ArF Excimer Laser Ablation", 1993, Applied Optics, 32:488-493.
Pettit et al. "Excimer Laser Ablation of the Cornea", 1995, Optical Engineering, 34:661-667.
Ediger et al. "Transmission of Corneal Collagen During ArF Excimer Laser Ablation", 1993, Lasers in Surgery and Medicine, 13:204-210.

* cited by examiner

*Primary Examiner*—A. Farah
(74) *Attorney, Agent, or Firm*—Akerman Senterfitt; Neil R. Jetter

(57) ABSTRACT

A laser-based refractive surgery system includes a laser source including a laser controller, wherein at least a portion of the incident beam is directed to target eye tissue of a patient. The incident beam portion produces a reflected beam after striking the eye tissue. The system includes at least one detector for detecting the reflected beam. A computer or data processor is communicably coupled to the detector and the laser controller. The computer or data processor generates a cross-correlation function using a plurality of discrete points which digitally represent a waveform representation of the reflected beam and a plurality of reference points. The reference points are preferably associated with a digital representation of the incident beam. The laser controller receives and utilizes the cross-correlation function or parameter derived therefrom, or the ablation rate, and adjusts at least one operating parameter of the laser beam in real-time during a refractive procedure.

18 Claims, 8 Drawing Sheets

SYSTEM AND METHOD FOR REAL-TIME FEEDBACK OF ABLATION RATE DURING LASER REFRACTIVE SURGERY

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The invention relates to laser refractive surgery, more particularly to methods for real-time feedback during laser refractive surgery and related systems.

BACKGROUND

Laser corneal refractive procedures, including photorefractive keratectomy (PRK) and laser-assisted in situ keratomileusis (LASIK), have become popular for the correction of imperfect vision conditions, such as myopia and/or astigmatism. These procedures involve the distribution of carefully controlled laser pulses over the treatment zone to reshape the corneal surface, which alters the refractive power and shifts the focal point of the cornea. Clinical laser systems are technologically advanced and very precise in many ways, allowing removal of corneal tissue with submicron accuracy. However, presently, the precision of refractive measurements exceeds the precision of tissue removal via ablation, hence real-time monitoring and control of the ablation rate remains a needed technology.

However, the hydration state of the eye, the healing response of the particular patient, the mechanics of the retina and other factors affect the results obtained. Furthermore, the refraction is conventionally achieved through a pre-computed process that attempts to account for all of the various factors. However, the pre-computed processing is entirely, or at least primarily, based on large patient population averages. The goal is to provide a process that achieves the desired change of refraction while minimizing the optical aberrations of the ocular system. However, in many cases the refractive surgery itself introduces significant aberrations. This may be due to either a change in the bio-mechanical structure, due to the edge of the treatment zone, due to variations in the actual patient-to-patient ablation rates, or due to variations across an individual cornea.

A number of instruments have been developed that have served as diagnostics for this process. These includes subjective and auto-refraction, corneal topography, pachymetry, and wavefront aberrometry. However, there are still variables that cannot be properly monitored that affect the outcome. In particular, factors such as the hydration state of the eye and healing response are difficult to account for in advance. The ablation profile for LASIK has long been known to be non-linear and have a different strength for positive or negative corrections. The ablation algorithms have been developed to take this into account, but there is still considerable variation from subject to subject because of largely unknown factors.

If the diagnostics could be applied in real time during the refractive surgery, some of this variation could be removed. This would allow the laser surgery to operate in a closed-loop mode, with the amount of refractive modification being monitored and controlled during the procedure. While it may be possible to monitor the change in shape of the cornea in "real-time" with corneal topography or other surface measurement apparatus, this only indirectly affects the total optical path and hence the refraction and higher order terms.

Frey, Burkhalter, Zepkin, Poppeliers and Campin in U.S. Pat. Nos. 6,271,914 and 6,271,915 disclose a method for ablating corneal material while monitoring the process in real time using a Hartmann plate sensor. Unfortunately, their techniques rely on modifying directly the optical zone that is measured. During the LASIK or PRK procedures that use ablation of portions of the cornea, the process of ablating material leads to unknown and undetermined optical scattering and effects during the ablation process. The surface of a dry cornea (needed for properly controlled ablation) or the interior surface that is exposed during the LASIK procedure are inherently rough. Thus these surfaces would scatter the injected and reflected light that is used for monitoring the wavefront. This significantly degrades the quality of the information obtained, making the aim difficult to achieve.

Published U.S. Application No. 20030174281 to Herekar et al. discloses a refractive control system including a laser refractive surgery instrument for modifying the refraction of the eye, an objective diagnostic apparatus for measuring the refraction and aberrations of the eye, and an aperture-sharing element to inject a refractive surgery beam and a monitoring diagnostic beam. Information regarding the refraction of the eye during surgical procedures is used to force the laser system to shut off when the desired refraction is achieved. Although Herekar et al. seek to take advantage of optical aberrations to provide feedback, they acknowledge that "in many cases the refractive surgery itself introduces significant aberrations" and that there is "a significant difficulty with incorporating the diagnostics into the lasers that are used for LASIK or PRK" because of obvious optical aberrations that are realized in these procedures. They further state that "while it may be possible to calibrate for these effects, it certainly falls short of the goal of directly measuring the desired result in real-time during the procedure." Accordingly, Herekar et al. relates to endpoint determination, and regarding the admittedly deficient real time feedback embodiment, does not disclose or suggest real-time feedback based on ablation rate, or a parameter correlated with the ablation rate.

SUMMARY

A laser-based refractive surgery system comprises a laser source including a laser controller for providing an incident laser beam, wherein at least a portion of the incident beam is directed to target eye tissue of a patient. The incident beam portion produces a reflected beam after striking the eye tissue. The system includes at least one detector for detecting the reflected beam. A computer or data processor is communicably coupled to the detector and the laser controller. The computer or data processor generates a cross-correlation function using a plurality of discrete points which digitally represent a waveform representation of the reflected beam and a plurality of reference points. The reference points are preferably associated with a digital representation of the incident beam.

The computer or data processor is provided a correlation between the cross-correlation function or a parameter derived therefrom with an ablation rate of eye tissue, such as based on data compiled prior to the surgery. The laser controller receives and utilizes the cross-correlation function or parameter derived therefrom, or the ablation rate, to adjust at least one operating parameter of the laser beam or the treatment algorithm in real-time during a refractive procedure. Thus, changes in actual laser ablation rates can be obtained and compensated for, including changes in ablation rate with respect to the clinically used large-patient pool average values. The invention thus provides an enhanced photorefractive system that provides more precise tissue ablation by measuring the real-time ablation rate or a parameter related thereto using an appropriate feedback signal.

The system can include a beam splitter or beam sampler for separating a sampled portion of the incident beam. In this embodiment, the at least one detector can comprises a first and a second detector, where the first detector detects the reflected beam and the second detector detects the incident beam.

In one embodiment of the invention, only a single detector is used. In this embodiment, the single detector can detect the reflected beam and a real time sampling of the incident beam. A computer or data processor can be used to deconvolve the waveform associated with the reflected beam from a waveform representing the incident beam which may generally overlap. A servo control or rotating mechanism can be provided for coupling to at least one optical component in the system. The servo control or rotating mechanism provides at least two positions, a first position moving the optical component to collect a waveform associated with the reflected beam at the single detector, and a second position moving the optical component to collect a waveform associated with the incident beam at the single detector.

The cross-correlation function can be generated by averaging a plurality of reflected and incident beams acquired over a plurality of laser pulses. In one embodiment, the cross correlation function is given by:

$$\langle R(0)I(\tau)\rangle \cong \frac{1}{\langle I(0)I(0)\rangle} \sum_{j=1}^{N} R_j I_{j+n}.$$

However, more generally, a cross correlation function is defined herein as a function derived from a plurality of discrete points that represent a reflected waveform from tissue and a plurality of discrete points that represent a reference waveform, or functions or quantities derived from the correlating the respective plurality of points.

The parameter derived from the cross-correlation function can comprise a decay slope of the cross correlation function. The decay slope can be correlated with the ablation rate during the refractive procedure.

A method of adjusting a refractive procedure for an eye, comprises the steps of performing a procedure to modify the refraction of the eye using a laser source which provides an incident laser beam, while the procedure is being performed, measuring a reflected beam reflected from the eye, and computing a cross-correlation function using a plurality of discrete points which digitally represent a waveform representation of the reflected beam and a plurality of reference points. The cross-correlation function or a parameter derived therefrom, or an ablation rate derived from the cross-correlation function is used to adjust at least one operating parameter of the laser source in real-time during the refractive procedure. The adjustment of the operating parameter is used to change the ablation rate or treatment algorithm. The reference beam can comprise a digital representation of the incident beam. The at least one operating parameter can comprise a number of laser pulses delivered or an energy of the incident laser beam. The cross-correlation function can be generated by averaging a plurality of the reflected and incident beams acquired over a plurality of laser pulses.

BRIEF DESCRIPTION OF THE DRAWINGS

A fuller understanding of the present invention and the features and benefits thereof will be obtained upon review of the following detailed description together with the accompanying drawings, in which.

DETAILED DESCRIPTION

Figure 1:
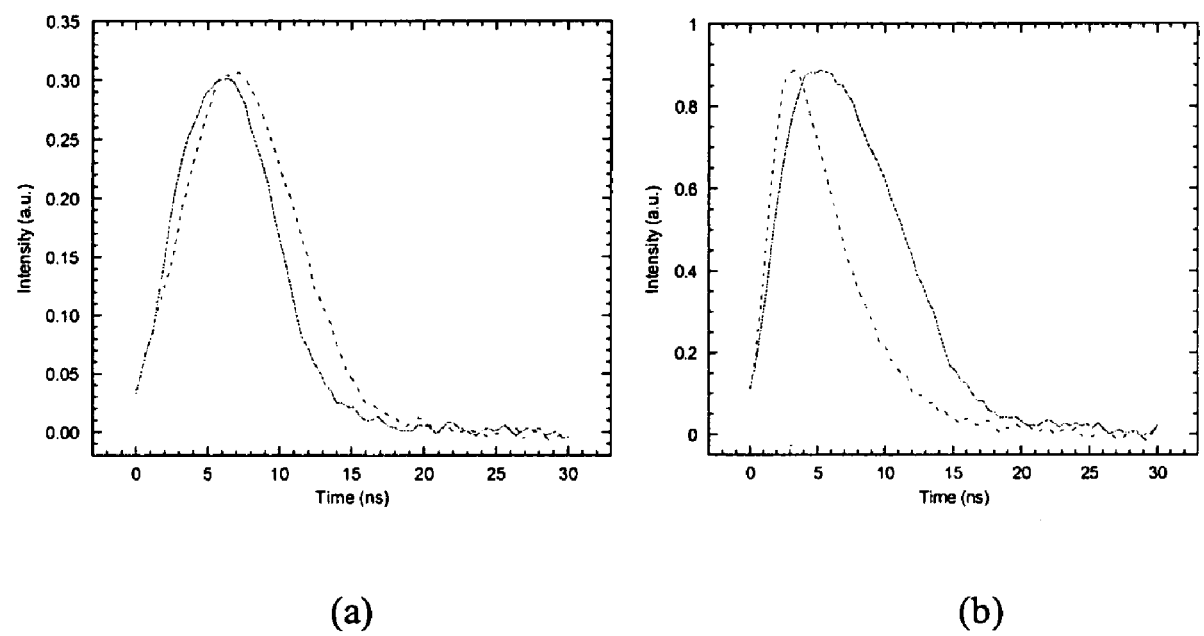
FIGS. 1(a) and (b) show incident and reflected pulses for sub-ablative and ablative cases, respectively. The dashed lines represents the reflected waveform.

A method and associated refractive surgery system allows measurement of the ablation rate or a parameter related thereto in real-time during laser refractive surgical procedures. Based on a desired ablation profile input and ablation map based on an assumed ablation rate conventionally provided, the invention provides real-time adjustment of the ablation rate during the refractive procedure based on feedback of the actual ablation rate or a calculated metric correlated to the actual ablation rate. Real-time adjustment of the ablation rate during the refractive procedure enables the desired ablation profile to be more closely achieved as compared to conventional refractive surgery systems and known improvements disclosed to date.

A laser-based refractive surgery system comprises a laser source including a laser controller for providing an incident laser beam, wherein at least a portion of the incident beam is directed to target eye tissue of a patient. The incident beam portion produces a reflected beam after striking the eye tissue. The system includes at least one detector for detecting the reflected beam. A computer or data processor is communicably coupled to the detector (such as through a digital oscilloscope) and the laser controller. The computer or data processor generates a cross-correlation function using a plurality of discrete points which digitally represent a waveform representation of the reflected beam and a plurality of reference points associated with a digital representation of the incident beam.

The computer or data processor is provided a correlation between the cross-correlation function or a parameter derived therefrom with an ablation rate of eye tissue. The correlation is generally based on data acquired and compiled prior to the surgery. The laser controller receives and utilizes the cross-correlation function or parameter derived therefrom, or the ablation rate, and adjusts at least one operating parameter of the laser beam in real-time during a refractive procedure. The invention thus provides an enhanced photorefractive system that provides more precise tissue ablation by measuring the real-time ablation rate or a parameter related thereto using an appropriate feedback signal.

This technique can be implemented in clinical systems to provide ablation rate feedback, which allows ophthalmic surgeons to compensate for ablation rates which differ from the expected ablation rate during the laser procedure. The expected ablation rate is generally derived from large patient population averages. Measurement or estimation of the actual ablation rate allows adjustment of laser source parameters, such as number of laser pulses delivered and/or the laser pulse energy, to correct for variations in the ablation rate when there is actual divergence from the expected ablation rate. Another advantage of the invention is that systems according to the invention are passive in nature, generally making use only of a sampling of the incident ablating laser pulse and the beam after reflection from the target eye tissue.

It is known that during a laser ablation correction event, there is a transient decrease in reflectivity of the targeted corneal tissue, an effect that is referred to as "truncation" of the reflected pulse of light. This truncation represents the physical and chemical interaction of the laser beam with the corneal tissue during the time course of the nominal 10-ns laser pulse. However, when the laser fluence (energy per unit area) is insufficient to cause ablation, ideally no truncation exists and the beam shape and structure of the reflected pulse is similar to that of the incident pulse of laser light. A representative comparison of incident and reflected pulses for the sub-ablative and ablative cases is shown in FIGS. 1(a) and 1(b), respectively. The dashed lines represent the reflected waveform in both cases.

In prior publications, researchers have attempted to quantify the reflected pulse truncation using various metrics, including the full-width half-maximum (FWHM) of the reflected pulse and a ratio of the FWHM of the reflected pulse to that of the incident pulse. However, these methods suffered from a lack of precision and responsiveness, such as the response slope. Specifically, the degree of actual change in the FWHM over relevant conditions being generally on the order of 10% is not sufficient to provide a strong enough response given the overall precision of the data. Techniques such as those reported that make use of a single metric to characterize the waveform (i.e. the FWHM, the integrated peak area, or the maximum intensity) fundamentally are limited from the total information that is contained in the plurality of sampled points that characterize the actual waveform. See, for example, M. N. Ediger, G. H. Pettit, R. P. Weiblinger, "Noninvasive monitoring of excimer laser ablation by time-resolved reflectometry" Refractive & Corneal Surgery, Vol. 9, pp. 268–275 (1993). As a result, no useful method based on pulse truncation before the invention resulted because the attainable sensitivity was insufficient to be useful in clinical systems.

Figure 2:
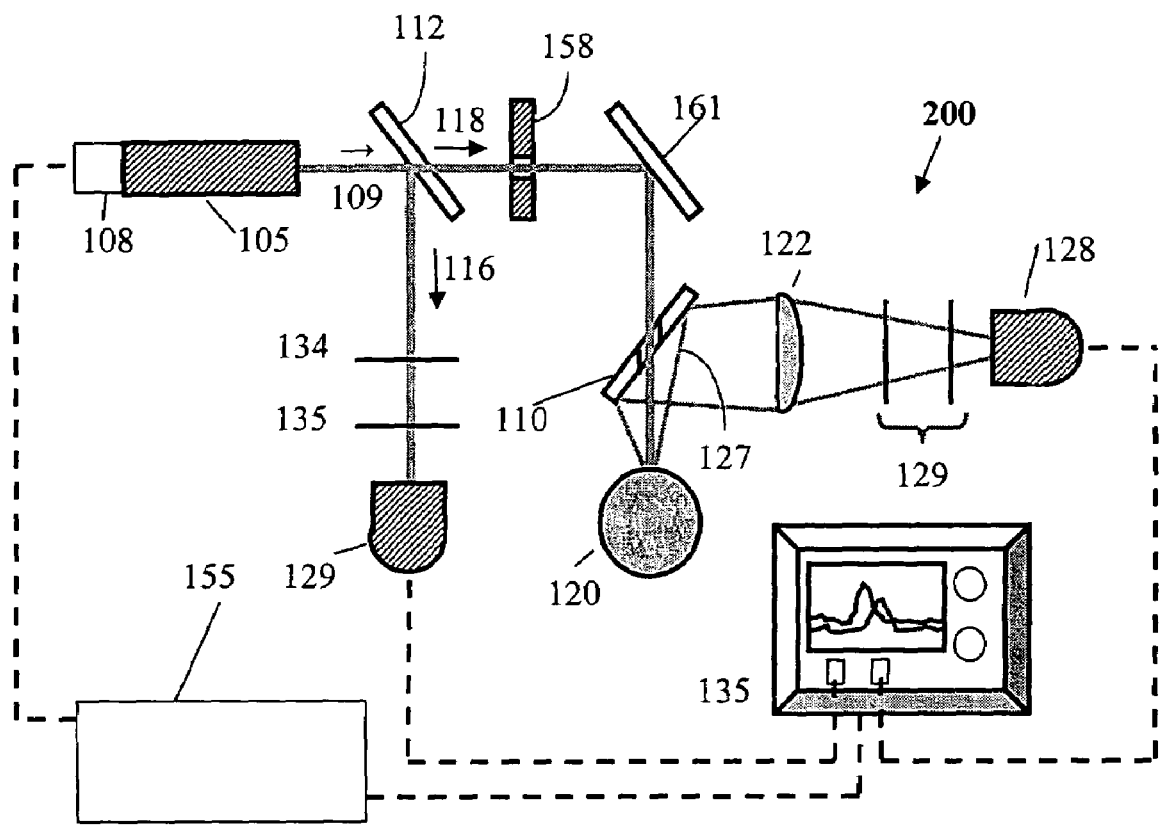
FIG. 2 shows a schematic of an exemplary laser refractive surgery system having dual detectors, according to an embodiment of the invention.
Figure 3:
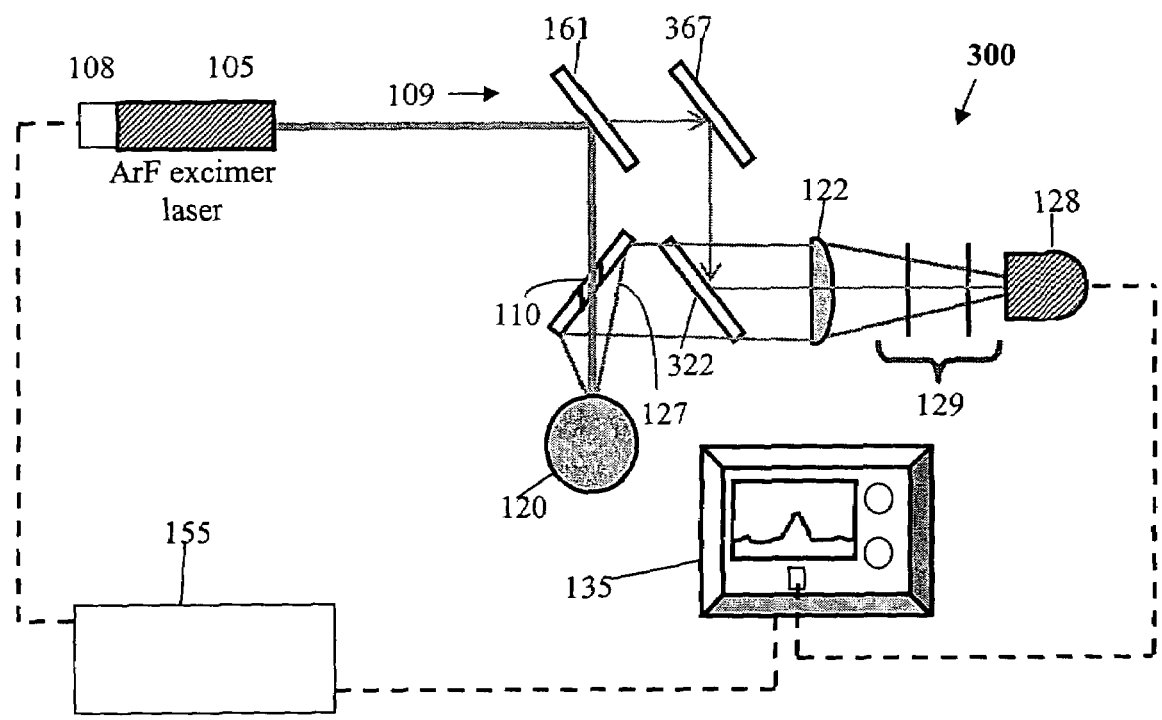
FIG. 3 shows a schematic of an exemplary laser refractive surgery system having a single detector configuration with a real-time reference measurement arrangement.
Figure 4:
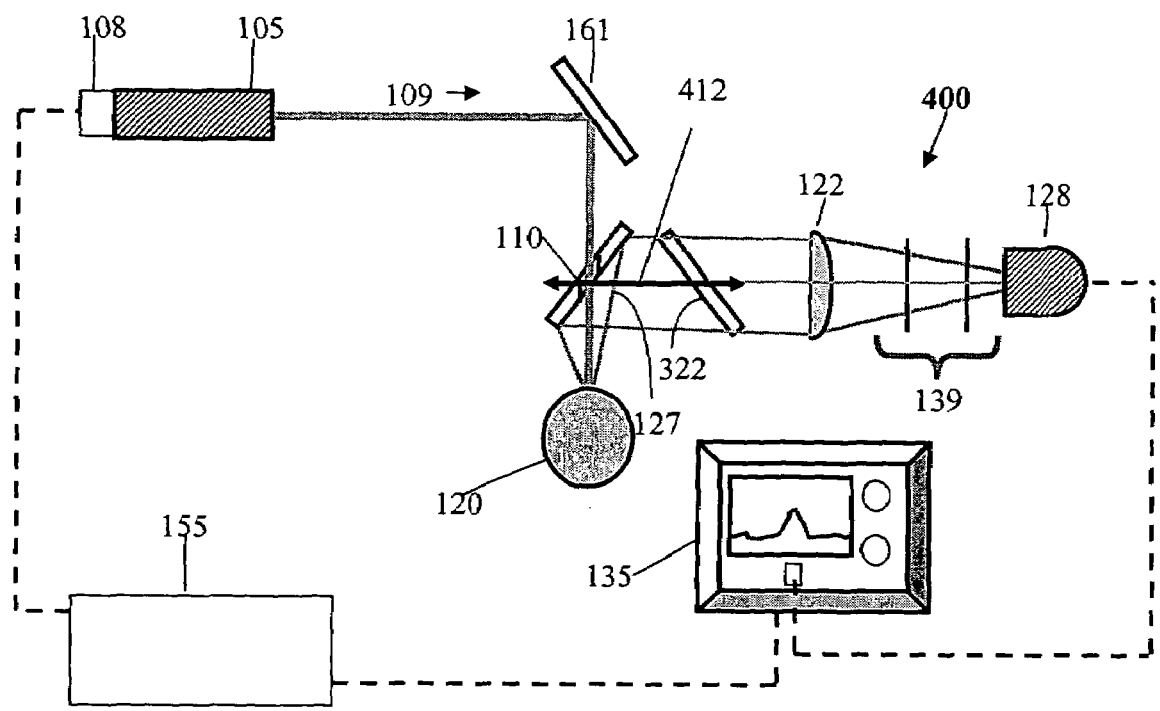
FIG. 4 shows a schematic of an exemplary laser refractive surgery system having a single detector configuration which utilizes pre-sampled reference measurements.

FIGS. 2–4 described below show exemplary system embodiments according to the invention. Although specific components are shown and described relative to FIGS. 2–4, it is noted that the waveform collection instrumentation may comprise any combination of mirrors, lenses, fast photodetectors, and signal processing equipment, including conventional commercially available optical and signal processing equipment.

FIG. 2 shows a schematic of an exemplary laser refractive surgery system 200 having dual detectors, one detector 128 for detecting the reflected pulse and a second detector 129 for detecting the incident pulse. Laser source 105 is provided for generating laser beam pulses 109. Laser controller 108 is associated with laser source 105. Quartz wedge 112 functions as a beam sampler which splits laser beam pulse 109 into beam 116 and another beam portion 118. Beam portion 118 passes through shutter 158 and is then reflected off mirror 161. Beam sampler 112 can be replaced by a beam splitter. Pierced mirror 110 transmits beam portion 118 to target eye 120 and also collects laser light reflected by target eye 120. Pierced mirror 110 could be replaced with optical flat or optical wedge. After being focused by focusing lens 122 and passing through matched filters 139 which provide attenuation, the reflected beam 127 is detected by photodetector 128. Photodetector 128 is preferably a fast rise time (~200 ps) detector. A fast, digitizing oscilloscope 135 (~2.5 Gs/s) is communicably connected to photodetector 128 to capture and digitize the reflected waveform. Digital oscilloscope 135 can be replaced with A/D data acquisition card.

Beam 116 is also detected using incident pulse detector 129, which is preferably also a fast rise time (~200 ps) detector. Neutral density filter 134 is provided for beam attenuation and 193 nm interference filter 135 is provided for eliminating fluorescence from the corneal tissue, preferably being provided in the path of incident beam prior to detection by detector 129. Computer/data processor 155 (e.g. PC) is communicably connected to laser controller 108 and detectors 128 and 129 through digital oscilloscope 135 to process the digitized incident and reflected waveforms. Although shown as separate units, digital oscilloscope 135 can be integrated with computer/data processor 155.

As described in more detail below, computer/data processor 155 generates a cross-correlation function using a plurality of discrete points which digitally represent a waveform representation of the reflected beam and a plurality of reference points associated with a digital representation of the incident beam. The computer or data processor is provided a correlation between the cross-correlation function or a parameter derived therefrom with an ablation rate of eye tissue. The correlation is generally based on data acquired and compiled prior to the surgery. The laser controller 108 receives and utilizes the cross-correlation function or parameter derived therefrom, or the ablation rate fed back, to adjust at least one operating parameter of the laser beam in real-time during a refractive procedure.

FIG. 3 shows a schematic of an exemplary laser refractive surgery system 300 having a single detector configuration with a real-time reference measurement arrangement. System 300 utilizes only a single fast-response detector and appropriate collection optics to capture both the incident and reflected waveforms together. An appropriate deconvolution technique known in the art can be used to separate the two waveforms. Like components shown in FIG. 2 are labeled the same.

Laser pulse 109 is sampled using leakage from the first 193-nm turning mirror 161. Quartz wedge 322 functions to inject the sampled incident beam into the optical path of the detector 128. Pierced mirror 110 could be replaced with optical flat or optical wedge. As noted above, digital oscilloscope 135 can be replace with A/D data acquisition card.

The waveform collected by detector 128 in system 300 is a convolution of the incident and reflected waveforms, which are separated in time by the difference in optical path delay, and which may generally overlap. Analogous to system 200, system 300 generates a cross-correlation function using a plurality of discrete points which digitally represent a waveform representation of the reflected beam and a plurality of reference points associated with a digital representation of the incident beam, and uses the cross correlation data fed back to adjust at least one operating parameter of the laser beam in real-time during a refractive procedure.

FIG. 4 shows a schematic of an exemplary laser refractive surgery system 400 having a single detector configuration which utilizes pre-sampled reference measurements. As before, like components shown in FIGS. 2 and 3 are labeled the same. Pierced mirror 110 and quartz wedge 322 functioning as a beam sampler are shown linked to a servo control, as shown by black arrow 412 in FIG. 4. The servo 412 moves the pierced mirror 110 out of the main laser beam path and the quartz wedge 322 into the main laser beam path to collect a reference waveform. The linear servo control 412 can be replaced with a rotating mechanism.

The servo 412 also moves the pierced mirror 110 into the main laser beam path and the quartz wedge out of the main laser beam path (as shown), to collect the reflected waveform. The rate of servo operation may vary to select any number of sampling rates, for example, alternate laser pulses between reference and reflected, to a rate of one reference to every 10 reflected pulses, to the limiting case of a reference pulse recorded before and/or after the laser procedure.

The measured reference waveform is then used with the real-time reflected waveform to perform the cross-correlation. As with the other systems, the cross correlation information fed back is used to adjust at least one operating parameter of the laser beam in real-time during a refractive procedure.

For system according to the invention, such as the exemplary ones shown in FIGS. 2–4, the direct collection optical paths could be replaced with fiber optics. In addition, the beam splitters and beam samplers could be replaced with direct viewing of the laser spot via a lens-coupled or fiber-optic coupled system.

In a preferred embodiment of the invention, a mathematical cross-correlation technique is used to process the incident and reflected waveforms. The cross-correlation technique according to the invention allows the truncation effect to be quantified and amplified by using a plurality of discrete points, and to identify a metric that can be correlated with the actual ablation rate of the corneal tissue in real time during the refractive surgery procedure. Using I(t) to represent the incident pulse 109, which is sampled via beam 116, and R(t) to represent the reflected pulse 127, from target eve 120, and also recognizing that the pulses consist of discrete data points when collected by a digital oscilloscope 135, the general form of a preferred cross-correlation function is as follows:

$$\langle R(0)I(\tau) \rangle \cong \frac{1}{\langle I(0)I(0) \rangle} \sum_{j=1}^{N} R_j I_{j+n} \quad (1)$$

As noted above, more generally, a cross correlation function is defined herein as a function derived from a plurality of discrete points that represent a reflected waveform from tissue and a plurality of discrete points that represent a reference waveform, or functions or quantities derived from the correlating the respective plurality of points. In a preferred embodiment, such as the cross correlation function shown above, the reference waveform is derived from a digital representation of the incident waveform pulse.

The above cross correlation function includes the optional normalization term $I(0)^2$, which is essentially the sum of the squares of the incident pulse values. Normalization generally enhances precision by ensuring that the cross-correlation function is affected only by the relative shapes of the incident and reflected pulses, and not by their absolute intensities.

However, in other embodiments, the reference waveform representation can be a constant, or more preferably a variable other than a variable derived from an incident waveform. The variable is preferably updated frequently, such as in real-time. In one embodiment, the reference waveform can be based on the time average of the reflected waveform, or a large patient population average reflected waveform.

The preferred cross-correlation function shown above is a function of the parameter $\tau$, which is the imposed temporal delay, implemented in software (such as the Matlab code provided in the Examples) processing preferably using the totality of points from the fully digitized waveform between the incident (I) and reflected (R) pulses for evaluation of the cross-correlation. The cross-correlation value is preferably determined at each $\tau$ by multiplying all of the corresponding data points of the two pulses together and summing those products.

Figure 5:
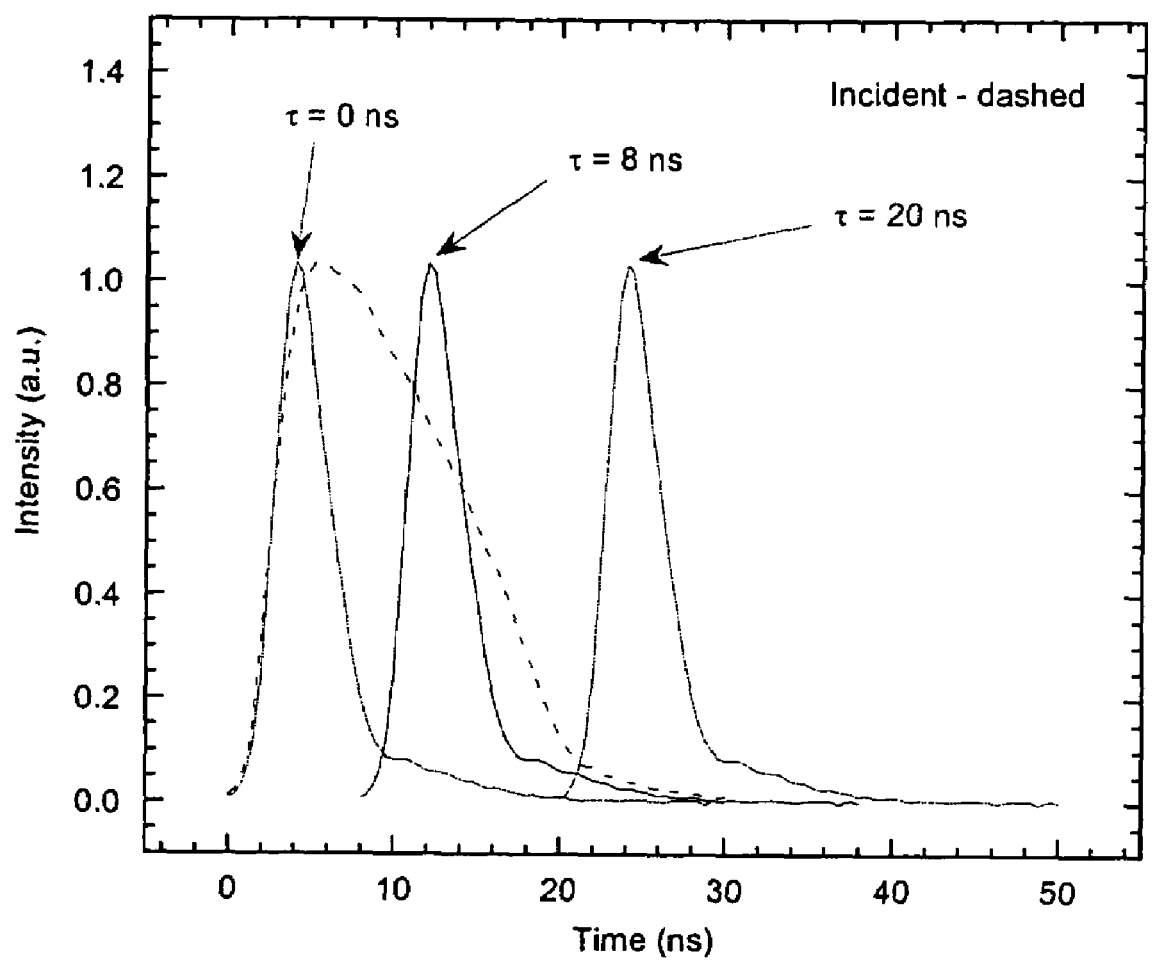
FIG. 5 is a graphical illustration which shows an exemplary cross-correlation curve shifting procedure. The dashed line represents the incident waveform. The solid lines represents the reflected waveforms for different values of introduced delay.

FIG. 5 is a graphical illustration which shows an exemplary cross-correlation curve shifting procedure. The dashed line represents the incident waveform. The solid lines represents the reflected waveforms for different values of introduced delay. For each value of tau ($\tau$), which represents the delay, the two curves (solid and dashed) are multiplied together point-by-point, with the result summed to represent to the cross-correlation function at that tau ($\tau$) value.

Figure 6:
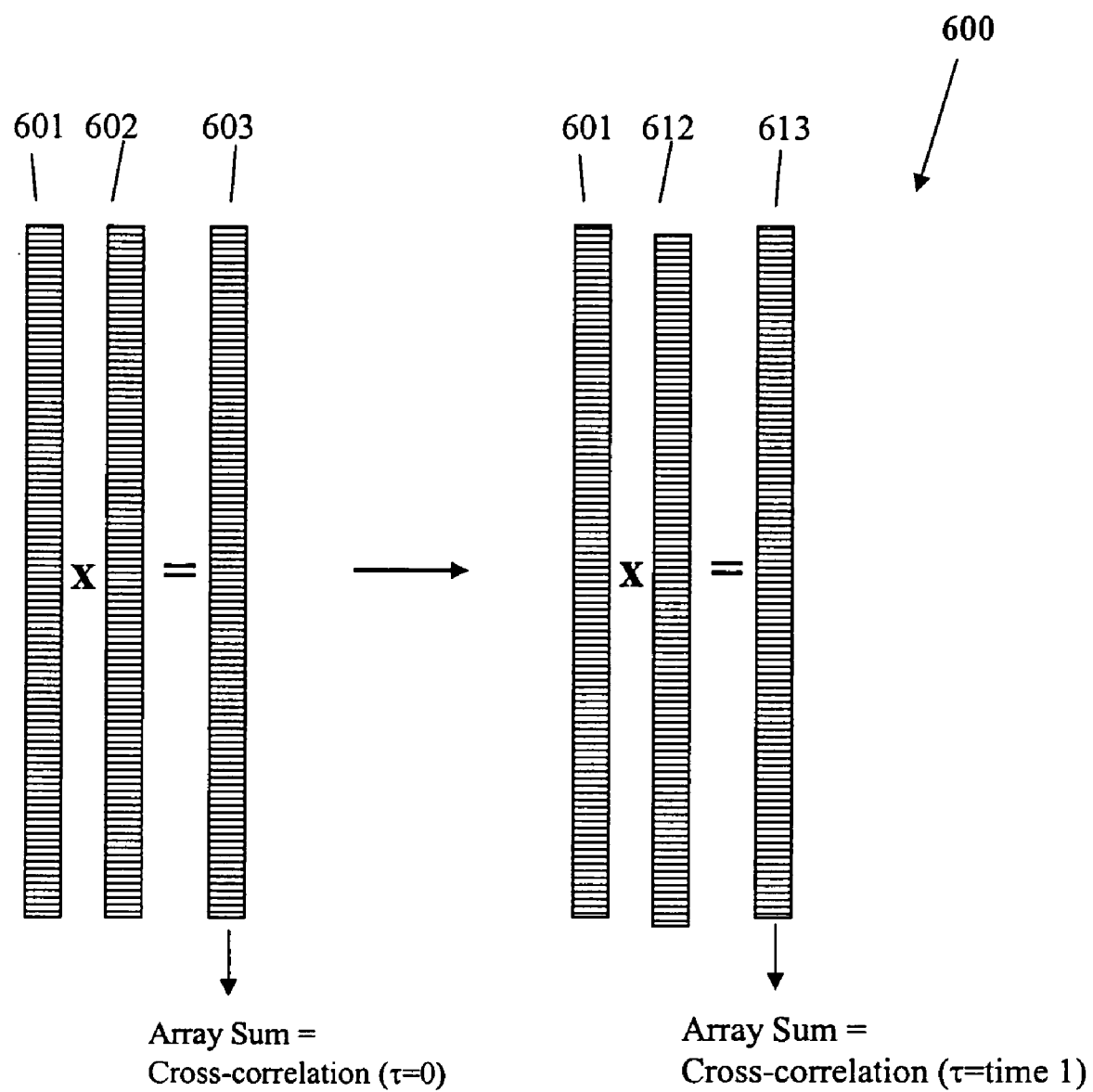
FIG. 6 is a schematic of an exemplary cross-correlation showing digital arrays of waveforms and the shifting of arrays to perform the cross-correlation function.

FIG. 6 is a schematic of an exemplary cross-correlation 600 showing digital arrays of waveforms and the shifting of arrays to perform the cross-correlation function. Reference 601 represents a 1-D array of a digitized reference waveform, 602 a 1-D array of digitized reflected waveform, and 603 represents a 1-D array of point-by-point product (shown by "X") of arrays 601 and 602. The summation of 1-D array 603 represents the cross-correlation corresponding to a delay value of zero. Reference 612 represents a 1-D array of a digitized reflected waveform, where each array element is shifted down one unit, where the shift is equal to the time between data points, which is referred to as tau. Reference 613 represents a 1-D array of the point-by-point product of 601 and 612. The summation of 1-D array 613 represents the cross-correlation corresponding to a delay value of tau. The process is preferably repeated by further shifting 612 down by one more unit, until the entire reflected array has been shifted the entire length of the array. For multiplication, all array elements of reference waveform 601 that do not match up with the array elements of reflected waveform 602 due to shifting are multiplied by zero.

Since the inventive technique provides an accurate assessment of the actual ablation rate and provides this information in real time, the implementation of this technique can provide real-time feedback of the true ablation rate for each individual patient, information which can then be used to adjust the treatment algorithm and ultimately result in a more accurate treatment and an improved surgical result. This novel technique is expected to improve the outcome for all patients undergoing excimer laser procedures. Furthermore, it is expected to improve the success rate for patients with extreme refractive conditions and lead to a decrease in the rate of retreatment. Elimination of re-treatment provides substantial cost-saving to clinical providers, and reduces risk to patient by eliminating the need for additional surgery.

A variety of products, services or commercial processes and other applications may result from this invention. Clinical laser refractive systems, used for procedures including, but not limited to, PRK and LASIK are already widely used. The inventive technique for real-time measurement of the corneal tissue ablation rate can be implemented into the clinical excimer laser system, for both new and existing systems. To obtain the necessary preferred measurements (incident and reflected pulses), only minor modifications are needed to existing clinical laser system.

The invention is expected to have medical uses beyond refractive surgery. For example, the invention can be used with any system that can benefit from the ability to accurately measure or estimate the ablation rate of material including tissue or material adhered to otherwise associate with tissue in real-time, or near real-time. For example, the invention can be applied to laser angioplasty systems. In such a system, two optical fibers are preferably used. A first fiber can deliver a beam to the treatment area while a second fiber can sample pick up the reflected beam from the treatment area. When a dynamic reference is desired for the cross correlation, the incident treatment beam can be sampled using one of the two fibers or an additional fiber, or as noted above, the reference waveform can be based on the time average of the reflected waveform, or a large patient population average reflected waveform.

EXAMPLES

It should be understood that the Examples described below are provided for illustrative purposes only and do not in any way define the scope of the invention. The data presented in the Examples demonstrates the ability of the invention to provide real-time information about the ablation rate of corneal tissue and through feedback use the information for real-time adjustment of the ablation rate during refractive procedures to more closely achieve a desired ablation profile.

Sample Matlab (MathWorks Natick, Mass.) code to perform cross-correlation according to the invention written by the inventors is provided below. The invention is in no way limited by the code or the particular algorithm implemented which is shown below.

```
%------------------------------------------------------------------------%
% Program: correlation.m
%
% Description:
% This program reads user-defined input text files (waveform data from the
% oscilloscope) and creates three output text files containing the properly aligned
% waveforms, the cross-correlation functions, and the initial and delay slopes of the
% cross-correlation funtions.
%------------------------------------------------------------------------%
clear
clc
delta = 1.6;        % default time delay (time lag between incident and reflected waveforms)
q = 0;              % initialize q to zero
while q == 0
    disp(' ')
        disp(['The default time delay is ',num2str(delta),' ns. Is this okay?'])
        check = input('\ny = yes, n = no ','s');
        if (check ~= 'y') & (check ~= 'n')                      % user input is not valid
        disp(' ')
        disp(' ')
    disp('     *** Error -- you must type y or n ***') % display error message
    disp(' ')
    % q remains zero
        elseif check == 'n'
        delta = input('\nNew time delay (in ns) = ');    % obtain new time delay
    q = 1;                                                          % change q to exit while loop
    else
        % default time delay is okay
        q = 1;                                                      % change q to exit while loop
    end
end                  % end 'while q == 0' loop
eye_start = input('\n\nFirst eye # = ');                % get user input
eye_finish = input('\nFinal eye # = ');                  % get user input
site_start = input('\nFirst site # = ');                  % get user input
num_sites = input('\nNumber of sites per eye = ')        % get user input
sitediff = site_start - 1;                  % calculate differential between first site # and index
q = 0;                                                                  % reset q to zero
while q == 0
    naming = input('\nHow are the files sequenced? (1=by shot #, 2=by site #) ');
    % get user input
    if (naming ~= 1) & (naming ~= 2)                        % user input is not valid
        % q remains zero
        disp(' ')
        disp(' ')
```

-continued

```
            disp('    *** Error -- your response must be either 1 or 2 ***')
                                                                        % display error message
            disp(' ')
        else
            q = 1;              % change q to exit while loop
        end
end                                     % end 'while q == 0' loop
disp(' ')
disp('------------------------------------------------------------')
disp(' ')
disp('Enter # of shots at each site (as a reference):')
for i = 1:num_sites
    sitenum = i + sitediff;                 % physical site #, related to index
    shots(i) = input(['\n# of shots at site ',num2str(sitenum),'= ']); % get user input
end
disp(' ')
disp('------------------------------------------------------------')
outfile1 = fopen('Waveforms.txt','wt');                 % open file for writing
outfile2 = fopen('Correlations.txt','wt');              % open file for writing
outfile3 = fopen('Slopes.txt','wt');                    % open file for writing
outfile4 = fopen('Sites.txt','wt');                     % open file for writing
% Write column headings:
fprintf(outfile3,'Eye Avg I Slope RSD (%%) Avg D Slope RSD (%%)\n');
fprintf(outfile3,'--- ----------- ------- ----------- -------\n');
fprintf(outfile4,'Eye Site I Slope D Slope Integrated Peak\n');
fprintf(outfile4,'--- ---- -------- --------- ---------------\n');
tau(1) = 3.2;
for i = eye_start:eye_finish
    for j = 1:num_sites
        sitenum = j + sitediff;                         % site #
        fprintf(outfile1,'Eye   Site   # Shots\n');     % write headings
        fprintf(outfile1,'%2d    %1d    %1d\n', i, sitenum, shots(j));
                                                        % write eye, site info
fprintf(outfile2,'Eye   Site   #Shots\n');              % write headings
fprintf(outfile2,' %2d    %1d    %1d\n', i, sitenum, shots(j));
                                                        % write eye, site info
if naming == 1                                          % create file prefix
            filepre = ['eye',num2str(i),'-',num2str(shots(j)),' wform '];
        else
    filepre = ['eye',num2str(i),'site',num2str(sitenum),' wform '];   % create file prefix
                                                        % create file prefix
end
wform = 0;                                              % initialize wform counter
for k = 5:19                                            % ignore first four ablation shots
    if k < 10
        filename = [filepre,'0',num2str(k)];    % concatinate filename
    else
        filename = [filepre,num2str(k)];        % concatinate filename
    end
    infile = fopen(filename,'rt');              % open file
    for l = 1:5
        header = fgetl(infile);                 % ignore first five lines of file
    end
    [wforms] = fscanf(infile,'%f');             % read waveform data
    fclose(infile);                             % close input file
    stop = length(wforms) / 2;                  % determine length of vector and
                                                %    calculate stopping point
    for l = 1:stop
        m = 2*l - 1;                            % index for incident wform
        n = 2*l;                                % index for reflected wform
        inc(l) = wforms(m);                     % create incident waveform vector
        ref(l) = wforms(n);                     % create reflected waveform vector
    end
    incmax = max(inc);                          % peak value of incident waveform
    maxpts = length(inc);                       % number of points in waveform
    for l = 1:maxpts
        if inc(l) == incmax
            peak = l;                           % location of peak maximum
            break
        end
    end
    if peak <= 40                               % not enough points before peak
        disp(' ')
            disp(['** Skipped file: ',filename,' (waveform cut off at left of screen)'])
        disp(' ')
        % do nothing, ignore waveform
```

```
else
    for l = 1:20
        rnoise(l) = ref(l);                         % first 20 points are noise
    end
rmsnoise = std(rnoise);                             % calculate rms noise value
refmax = max(ref);                                  % max value of reflected waveform
test = 15*rmsnoise;                                 % test for presence of legitimate
                                                    %    reflected waveform
if refmax < test                                    % want to skip this waveform
        disp(' ')
            disp(['** Skipped file: ',filename,' (no reflected waveform)'])
disp(' ')
% do nothing, ignore waveform
else                                                % reflected waveform is present
for l = 1:20
a(l) = inc(l);                                      % sub-vector of first 20 elements
end                                                 %    of incident waveform
avg = mean(a);                                      % average of sub-vector
dev = std(a);                                       % standard deviation of sub-vector
wftest = avg + 4*dev;                               % test value for leading edge of
                                                    %    incident waveform
for l = 1:maxpts
if inc(l) >= wftest                                 % at leading edge of waveform
    diff = maxpts - l;                              % determine how many points remain
    d = round(delta / 0.4);                         % round lag to nearest integer
    pts_need = 100 + d;
    if diff >= pts_need                             % enough points to get whole wform
    if inc(l+1) > inc(l)
        if inc(l+2) > inc(l+1)
        if inc(l+3) > inc(l+2)                      % 3 successively increasing points
                                                    %    indicates true leading edge
                    wform = wform + 1;              % increment # of waveforms
                    inc_base(wform) = avg;          % write avg of incident baseline
            for m = 1:101                           % includes data up to 40 ns    to a vector
                p = m + l - 1;                      % l is fixed, need a moving counter
                    wfinc(m,wform) = inc(p);        % aligned incident waveform
                wfref(m,wform) = ref(p+d);          % aligned reflected waveform
                    end
                break                               % exit 'for l=1:maxpts' loop if
                                                    %    waveform acquired
            end                                     % end 'if inc(l+3) > inc(l+2)'
            end                                     % end 'if inc(l+2) > inc(l+1)'
        end                                         % end 'if inc(l+1) > inc(l)'
    else                                            % not enough points to get whole wform
    disp(' ')
    disp(['** Skipped file: ',filename,' (waveform cut off at right of screen)'])
    disp(' ')
    break                                           % exit 'for l=1:maxpts' loop
                                                    % ignore waveform
            end                                     % end 'if diff >= 101'
        elseif l == maxpts                          % we are at the last point
        disp(' ')
        disp(['** Skipped file: ',filename,' (no incident waveform)'])
        disp(' ')
        % ignore waveform
end                                                 % end 'if inc(l) >= wftest'
end                                                 % end 'for l=1:maxpts' loop
end                                                 % end 'if refmax < test'
    % if wform >= 15
    % break                                         % exit 'for k=2:19'loop when six
                                                    %    good waveforms are acquired
        % end
    end                                             % end 'if peak <= 40'
end                                                 % end 'for k=5:19' loop
for k = 1:101
    isum = 0;                                       % initialize isum
    rsum = 0;                                       % initialize rsum
    for l = 1:wform
        isum = isum + wfinc(k,l);                   % sum incident waveform elements
        rsum = rsum + wfref(k,l);                   % sum reflected waveform elements
    end
    inc_avg(k) = isum / wform;                      % create avg inc wform vector
    ref_avg(k) = rsum / wform;                      % create avg ref wform vector
    fprintf(outfile1,'%10.8f %10.8f\n', inc_avg(k), ref_avg(k));
```

```
            end                                              % end 'for k=1:101' loop
        fprintf(outfile1,'\n');
        intsum = 0;                                          % initialize peak sum to zero
        for k = 1:101
            intsum = intsum + inc_avg(k);                    % evaluate integrated incident peak
        end
        norm = 0;                                            % initialize correlation normalizer
        for k = 1:101
            a2 = (inc_avg(k))^2;
            norm = norm + a2;                                % autocorrelation at tau = 0
        end
        r = 0;                                               % initialize r
        for k = 1:101                                        % sets tau value
            sum = 0;                                         % initialize sum
            r = r + 1;                                       % increment r to slide wforms
            for l = 1:101                                    % determines which point of ref
                                                             %    wform to use
                s = 1 + r - 1;                               % determines which point of inc
                                                             %    wform to use
                if s > 101
                    term = 0;                                % s exceeds size of waveform
                else
                    term = ref_avg(l) * inc_avg(s); % cross-correlation elements
                end
                sum = sum + term;                            % cross-correlation sum
            end         % end for l=1:101 loop
            corr(k) = sum * max(inc_avg) / max(ref_avg) / norm; % normalized cross-
                                                             %    correlation values
            fprintf(outfile2,' %8.6f\n', corr(k));
        end                                                  % end 'for k=1:101' loop
        islope(j) = (2*corr(4) - 9*corr(3) + 18*corr(2) - 11*corr(1)) / (6*0.4);
        % initial cross-correlation slope
        corrsub(1) = corr(9);
        for k = 1:13
            offset = k + 9;
            corrsub(k+1) = corr(offset);
            tau(k+1) = tau(k) + 0.4;
        end
        coeff = polyfit(tau,corrsub,1);
        dslope(j) = coeff(1);
            incpeak = intsum - (101 * mean(inc_base)); % calculate integrated incident peak
                                                             %   (baseline subtracted)
            fprintf(outfile4,'%1d  %1d   %8.6f %8.6f   %9.6f\n',i,sitenum,islope(j),dslope(j),incpeak);
        fprintf(outfile2,'\n');
    end                                                      % end 'for j=1:num_sites' loop
    fprintf(outfile4,'\n');
    avg_islope = mean(islope);                               % avg slope for all sites
    dev_islope = std(islope);                                % standard deviation of slopes
    rsd_islope = abs(dev_islope / avg_islope) * 100; % relative standard deviation
    avg_dslope = mean(dslope);
    dev_dslope = std(dslope);
    rsd_dslope = abs(dev_dslope / avg_dslope) * 100;
    fprintf(outfile3,'%1d   %8.6f   %7.4f  %8.6f   %7.4f\n',i,avg_islope,rsd_islope,avg_dslope,rsd_dslope);
end                                                          % end 'for i=eye_start:eye_finish'
                                                             %    loop
fclose(outfile1);      % close output file
fclose(outfile2);      % close output file
fclose(outfile3);      % close output file
fclose(outfile4);      % close output file
disp('-----------------------------------------------------------')
disp(' ')
disp(' ')
% END Program
```

Figure 7:
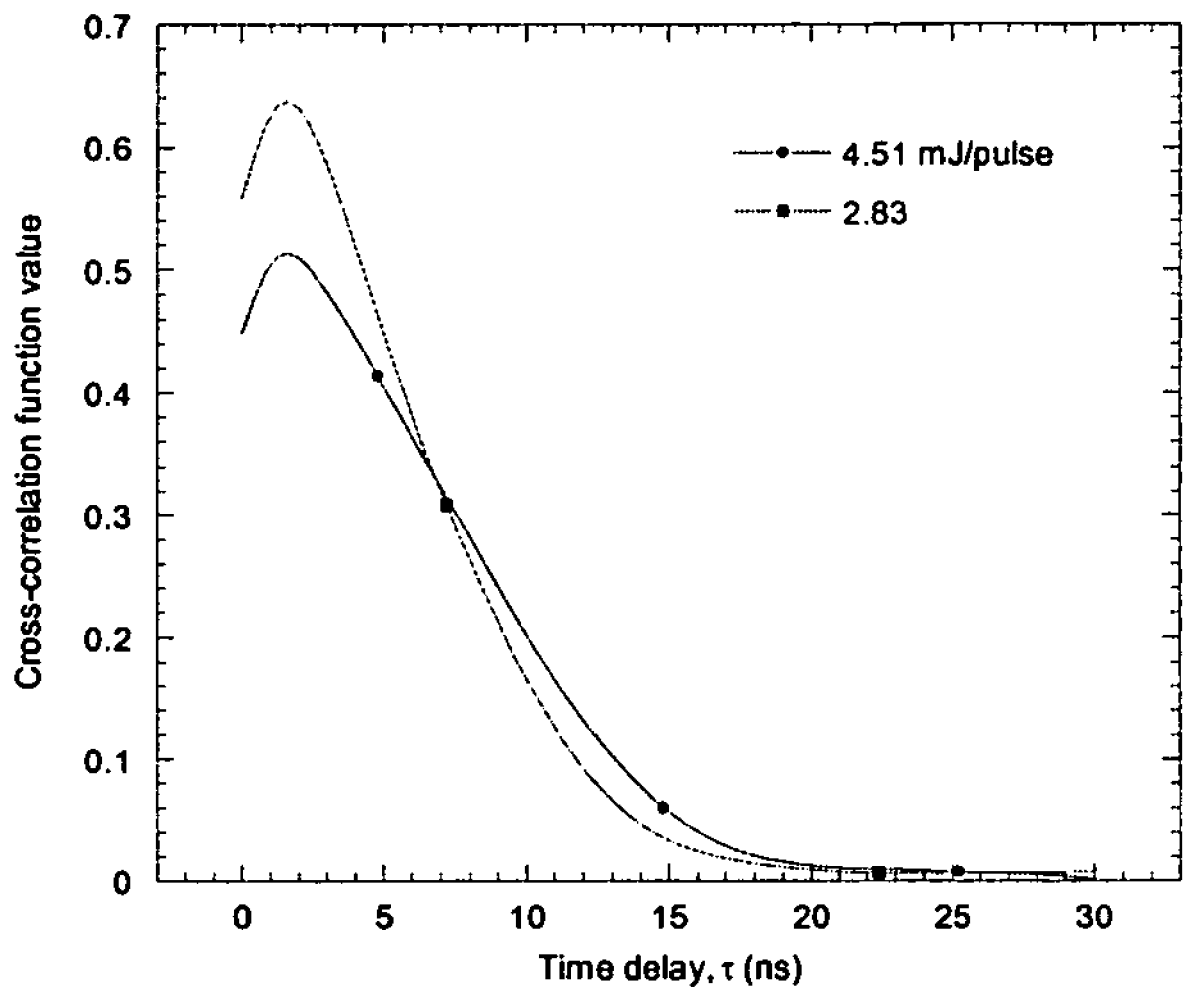
FIG. 7 shows the cross-correlation functions obtained for two different laser energy levels.

FIG. 7 shows the cross-correlation functions for two different laser energy levels. It is noted that the ablation rate for clinically relevant laser fluence scales with laser energy. These cross-correlation functions were derived from incident and reflected pulses that were averaged for laser pulses 2 through 20 of a 25-pulse sequence recorded during bovine corneal tissue ablation (for each energy).

Figure 8:
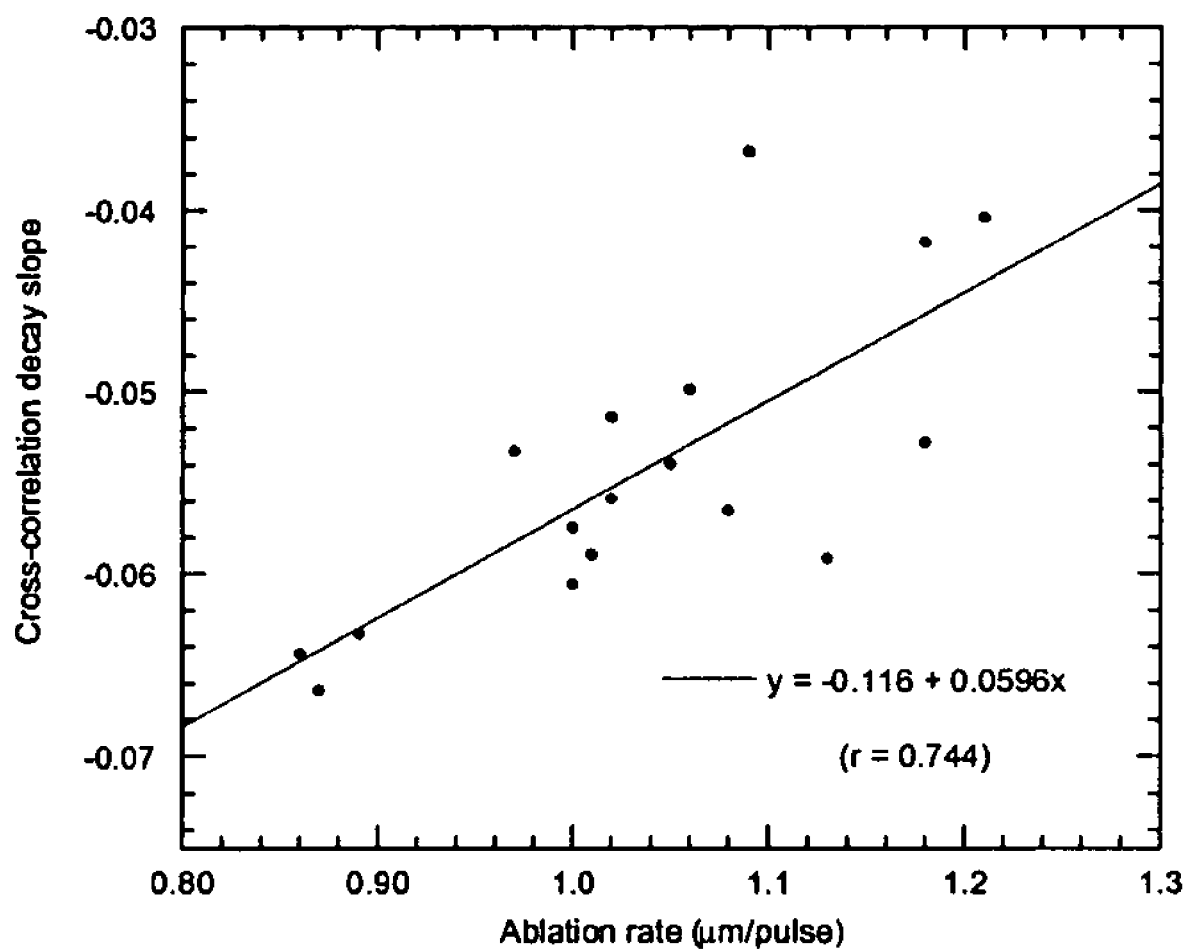
FIG. 8 shows a cross-correlation decay slope as a function of the corneal tissue ablation rate. By measuring the cross-correlation decay slope during refractive surgery, the corneal tissue ablation rate can be determined.

One helpful metric that can be derived from the cross-correlation function is the slope of the approximately linear, decaying portion of the profile. This "decay slope" can be determined by fitting a line, such as a least-squares line to the data. Referring to FIG. 8, least square lines are fit for the data points ranging from $\tau=3.2$ ns to $\tau=8.4$ ns, inclusive of the endpoints. For the cross-correlation functions corresponding to ablation at 2.83 mJ/pulse and 4.51 mJ/pulse, the decay slopes were determined to be negative 0.064 and negative 0.040, respectively. Therefore, the decay slope of the cross-correlation function responds to the expected change in ablation rate.

Ablation experiments were carried out in which incident and reflected pulses were recorded and the ablation rate measured for a range of laser energy levels. The true effective ablation rate was measured using a published technique (Fisher B. T., & Hahn D. W. Ophthalmic Surgery, Lasers & Imaging, January/February 2004; Vol. 35, No 1, 41–51). Determination of excimer laser ablation rates of corneal tissue was performed using wax impressions of ablation craters and white-light interferometry. At each ablation site, 25 to 30 laser pulses were delivered (depending on the laser energy), and the incident and reflected pulses were averaged for pulses number 2 through 20 of each incident laser pulse sequence. Therefore, a single cross-correlation function was formulated based on the average incident and reflected pulses at each ablation site, and the decay slope was extracted from each of these correlation functions as described above. FIG. 8 shows the decay slope as a function of the ablation rate, where each data point represents one ablation site.

It can be seen in FIG. 8 that the decay slope of the exemplary cross-correlation function increases monotonically and essentially linearly as the ablation rate increases. The scatter in the data is considered a result of precision issues associated with the determination of the tissue ablation rate via wax impressions. This definite, positive relationship between decay slope and ablation rate has important implications for clinical systems. With this data, it is demonstrated for the first time that experimentally that the decay slope of the auto-correlation function correlates directly with the laser ablation rate. Furthermore, it should be noted that the cross-correlation and the corresponding decay slope are derived from measurements of optical waveforms that are obtained passively, and do not affect the corneal tissue or ablation process in any way. Other portions or derivatives from the cross-correlation function can also be correlated positively with the ablation rate, for example, the slope of the leading edge of the cross-correlation function.

It should be understood that the Examples and embodiments described herein are for illustrative purposes only and that various modifications or changes in light thereof will be suggested to persons skilled in the art and are to be included within the spirit and purview of this application. The invention can take other specific forms without departing from the spirit or essential attributes thereof.

We claim:

1. A laser-based refractive surgery system, comprising:
   a laser source including a laser controller for providing an incident laser beam, wherein at least a portion of said incident beam is directed to target eye tissue of a patient, said incident beam portion producing a reflected beam after striking said eye tissue;
   at least one detector, said detector for detecting said reflected beam, and
   a computer or data processor communicably coupled to said detector and said laser controller, wherein said computer or data processor generates a cross-correlation function using a plurality of discrete points which digitally represent a waveform representation of said reflected beam and a plurality of reference points, said computer or data processor providing a correlation between said cross-correlation function or a parameter derived therefrom with an ablation rate of said eye tissue,
   wherein said laser controller uses said cross-correlation function, a parameter derived therefrom or said ablation rate, to adjust at least one operating parameter of said laser beam in real-time during a refractory procedure.

2. The system of claim 1, wherein said reference beam comprises a digital representation of said incident beam.

3. The system of claim 1, further comprising a beam splitter or beam sampler, said beam splitter or beam sampler separating a sampled portion of said incident beam, wherein said at least one detector comprises a first and a second detector, wherein a first detector detects said reflected beam and said second detector detects said incident beam.

4. The system of claim 1, wherein said at least one detector consists of a single detector.

5. The system of claim 4, wherein said single detector detects said reflected beam and a real time sampling of said incident beam.

6. The system of claim 5, wherein said computer or data processor deconvolves a waveform associated with said reflected beam from a waveform representing said incident beam.

7. The system of claim 5, further comprising a servo control or rotating mechanism coupled to at least one optical component in said system, said servo control or rotating mechanism providing at least two positions, a first position moving said optical component to collect a waveform associated with said reflected beam at said single detector, and a second position moving said optical component to collect a waveform associated with said incident beam at said single detector.

8. The system of claim 1, wherein said cross-correlation function are generated by averaging a plurality of said reflected and said incident beams acquired over a plurality of laser pulses.

9. The system of claim 1, wherein said cross correlation function is given by:

$$\langle R(0)I(\tau)\rangle \cong \frac{1}{\langle I(0)I(0)\rangle}\sum_{j=1}^{N}R_j I_{j+n}.$$

10. The system of claim 1, wherein said parameter derived therefrom comprises a decay slope of said cross correlation function.

11. A method of adjusting a refractive procedure for an eye, comprising the steps of:
    performing a procedure to modify the refraction of said eye using a laser source which provides an incident laser beam;
    while the procedure is being performed, measuring a reflected beam reflected from said eye; and
    computing a cross-correlation function using a plurality of discrete points which digitally represent a waveform representation of said reflected beam and a plurality of reference points, and
    using said cross-correlation function, a parameter derived therefrom or an ablation rate of said eye derived from said cross-correlation function to adjust at least one operating parameter of said laser source in real-time during said refractory procedure, adjustment of said operating parameter changing said ablation rate or treatment algorithm.

12. The method of claim 11, wherein said reference beam comprises a digital representation of said incident beam.

13. The method of claim 11, wherein said at least one operating parameter comprises a number of laser pulses delivered or an energy of said incident laser beam.

14. The method of claim 11, wherein a single detector is used to detect said reflected beam and said incident beam.

15. The method of claim 12, further comprising the step of deconvolving a waveform associated with said reflected beam from a waveform associated with said incident beam.

16. The method of claim 12, further comprising the step of moving between two positions during said procedure, a first position exclusively collecting a waveform associated with said reflected beam at said single detector, and a second position exclusively detecting a waveform associated with said incident beam at said single detector.

17. The method of claim 11, wherein said cross-correlation function is generated by averaging a plurality of said reflected and said incident beams acquired over a plurality of laser pulses.

18. The method of claim 11, wherein said cross correlation function is given by:

$$\langle R(0)I(\tau)\rangle \cong \frac{1}{\langle I(0)I(0)\rangle}\sum_{j=1}^{N} R_j I_{j+n}.$$

* * * * *